United States Patent [19]

Mercier

[11] 4,100,189

[45] Jul. 11, 1978

[54] RECOVERY OF ACETIC ACID FROM DILUTE AQUEOUS SOLUTIONS THEREOF

[75] Inventor: Jules Mercier, Melle-Deux-Sevres, France

[73] Assignee: Rhone-Poulenc Industries, Paris, France

[21] Appl. No.: 651,195

[22] Filed: Jan. 21, 1976

[30] Foreign Application Priority Data

Apr. 25, 1975 [FR] France .................................. 75 12799

[51] Int. Cl.² .......................... C07C 51/46; C07C 51/48
[52] U.S. Cl. ...................................... 260/541; 560/248; 560/265
[58] Field of Search ...................... 260/541, 540, 488 F

[56] References Cited

U.S. PATENT DOCUMENTS

| 1,860,553 | 5/1932 | Ricard et al. | 260/541 |
| 3,488,386 | 1/1970 | Rice, Jr. | 260/541 |
| 3,579,297 | 5/1971 | Ekblom | 260/541 |

*Primary Examiner*—Vivian Garner
*Attorney, Agent, or Firm*—Bacon & Thomas

[57] ABSTRACT

Acetic acid is recovered from its dilute aqueous solutions by extracting same with an organic solvent, neutralizing the acidic extract with aqueous ammonia, whereby there are separated an organic phase and an ammonium acetate containing aqueous phase, and thence thermally decomposing said ammonium acetate.

18 Claims, 1 Drawing Figure

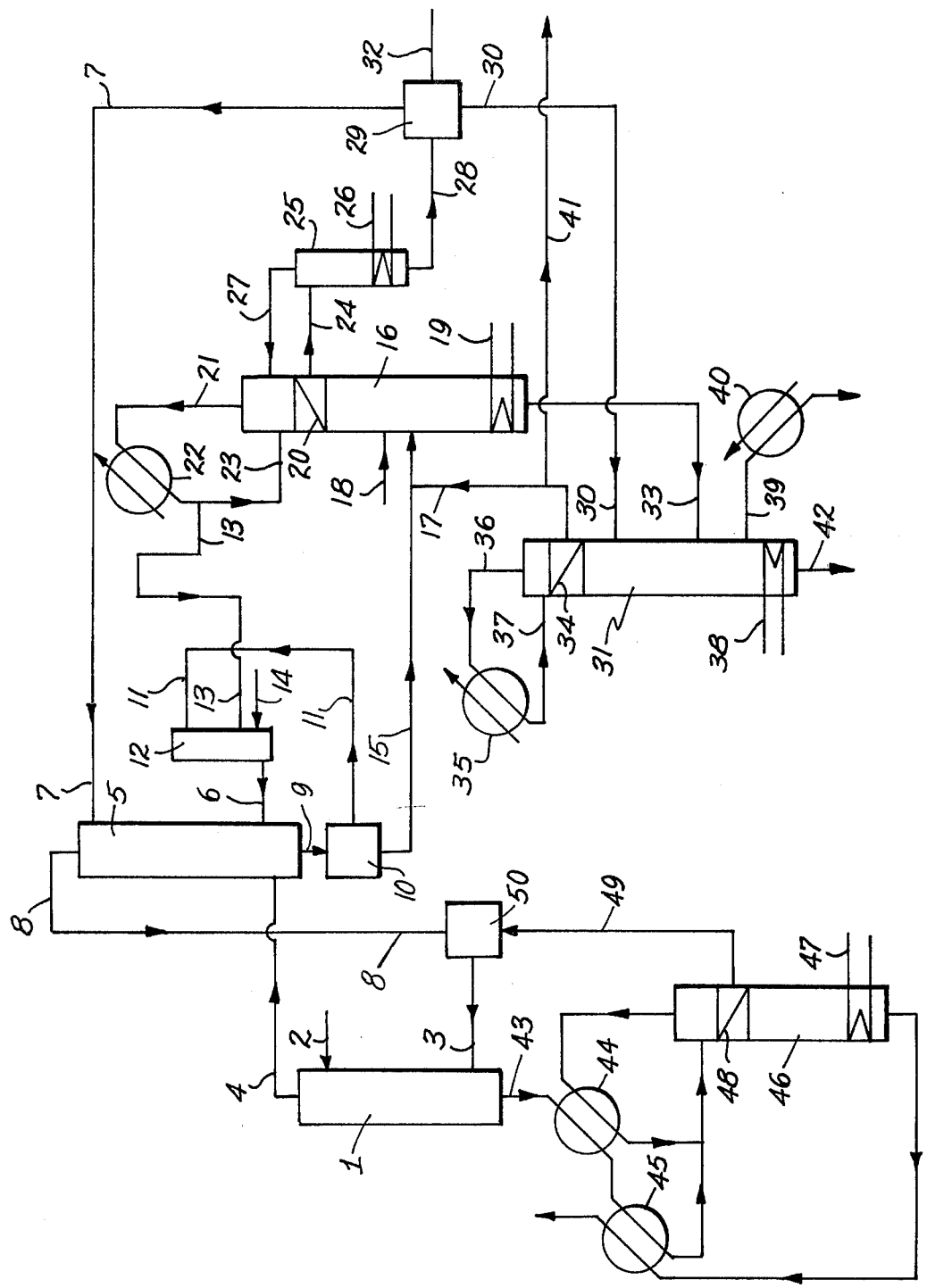

RECOVERY OF ACETIC ACID FROM DILUTE AQUEOUS SOLUTIONS THEREOF

BACKGROUND OF THE INVENTION

1. Field of the Invention

The present invention relates to an improved process for the recovery of acetic acid from very dilute aqueous solutions of same. By the term "dilute aqueous solutions" in the present specification and claims is meant aqueous solutions with an acid content of 0.5 to 3% by weight.

2. Description of the Prior Art

The known techniques for the recovery of acetic acid from its aqueous solutions generally consist of continuously extracting same, in the liquid phase, by means of a solvent selected both for its high coefficient of extraction of the subject acid and for its selectivity, namely, selected for the ratio of enrichment with acid relative to water content of the said solvent, and which is achievable with such solvent.

According to these known techniques, the extract layer, in which the concentration of the acid relative to water is generally greater than its concentration in the mixture to be treated, is subsequently continuously distilled to initially separate the acid in anhydrous state, and which no longer contains any solvent, and secondly and simultaneously, to separate by hetero-azeotropic distillation the hydrated and deacidified solvent and the water. The hydrated solvent is recycled to the extraction stage. The aqueous solution, from which the acid has been removed, is treated in an extraction column to recover dissolved solvent.

The solvent can be a single organic compound or a mixture of organic compounds.

For a given solvent, the economics of the separation stage, which stage reflects the relative amounts of acetic acid and water contained in the organic layer, depend, all other conditions being equal, on the concentration of acetic acid in the initial aqueous solution to be treated. As a result, the amount of heat energy to be provided in order to isolate the acetic acid from the acidic organic solvent layer is the higher, the lower being the initial concentration of the aqueous acetic acid solution which is to be extracted.

If the acid content is of the order of 1 to 3%, the cost of the heat energy and, correspondingly, the magnitude of the investment required becomes prohibitive, even to the point of exceeding the intrinsic value of the anhydrous acid thus obtained.

SUMMARY OF THE INVENTION

Accordingly, it is a primary object of the present invention to provide for the improved recovery of acetic acid from dilute aqueous solutions thereof.

Another object of the invention is to provide for the improved recovery of acetic acid from its dilute aqueous solutions by extracting such solutions with an organic solvent, neutralizing the acidic extract with aqueous ammonia, whereby there are separated an organic phase and an ammonium acetate containing aqueous phase, and thence thermally decomposing said ammonium acetate.

Other objects, features and advantages of the invention will become more apparent from the description which follows.

BRIEF DESCRIPTION OF THE DRAWING

The FIGURE of drawing is a schematic of the apparatus utilized in conducting the process according to the invention.

DETAILED DESCRIPTION OF THE INVENTION

It has now been determined that the foregoing objects of the invention are readily attained by a new process [in the course of the process for recovering acetic acid by solvent extraction] for isolating the acetic acid from the organic layer resulting from a typical extraction step. According to the invention, the acid extract is neutralized by the action of ammonia dissolved in an aqueous liquid, the ammonia being present in stoichiometric amount, and an aqueous ammonium acetate phase is thus formed which contains a portion of the water initially present in the acid extract.

The result is thus that an aqueous solution is obtained which is enriched in (potential) acetic acid relative to starting solution. The partition coefficient of ammonium acetate very much favors the aqueous phase and it is sufficient to wash the deacidified extraction solvent with a very small amount of water to free same essentially completely of ammonium acetate. Of course, this wash lowers the ammonium acetate concentration of the aqueous solution. However, the potential acetic acid concentration of this solution remains higher than the "potential acid/potential acid + water" concentration of the organic phase. Thus, by virtue of this wash, the solvent of extraction can be directly recycled to the extraction stage without it being necessary to consume heat to regenerate the solvent. In fact, not only is the solvent sufficiently pure to fulfil its function as an extraction agent, but also the traces of ammonium acetate which have escaped the wash are so small that they do not present the hazard of increasing the content of organic matter in the aqueous effluent from the extraction stage.

Another characteristic of the present invention resides in the technique for the thermal decomposition of the ammonium acetate, which consists of liberating the acetic acid while at the same time recovering the ammonia liberated, thus permitting the immediate recycle of the latter to the neutralization stage.

For this purpose, the decomposition of the ammonium acetate is conducted in a suitably heated distillation column, equipped with trays defining a reaction zone, and in the presence of a third component which forms, with the water, a heteroazeotrope of minimum boiling point, said thir component advantageously being identical to the solvent of extraction. Such distillation column is charged, at its midsection, with an aqueous solution of ammonium acetate and with a suitably predetermined amount of the third component which acts as an entraining agent. Depending on the temperatures prevailing in the column, the ammonium acetate can be decomposed within a residence time of 1 to 4 hours and the ammonia thus liberated is evolved as a top fraction.

Simultaneously, the water is entrained heteroazeotropically by the third component and is separated from the latter in a decanting tray inserted in the upper regions of the column, while anhydrous acetic acid is abtained as bottoms, in solution with the third component which is now in the role of solvent.

To achieve complete decomposition of the ammonium acetate when operating at atmospheric pressure, it is necessary to operate at a temperature range of between 90° and 130° C. and, more preferably, between 105° and 127° C. It is also of great importance to judiciously elect the third component to take into account the chemical nature of the system.

In fact, this third component must form, with water, a heteroazeotrope which is as rich as possible in water and which has a sufficiently high boiling point to permit easy and complete separation from the ammonia.

It must be capable of maintaining the not as yet decomposed ammonium acetate in solution in the finishing zone in the lower part of the column where the medium has become anhydrous or almost anhydrous, thus excluding hydrocarbons and ethers.

Same, further, must not react to form stable or irreversible compounds with ammonia under the reaction conditions; and this excludes compounds with a carbonyl group, such as the ketones and aldehydes.

It also must, under the operating conditions of the column wherein the ammonium acetate is decomposed, form a homogeneous liquid admixture with acetic acid, but this mixture must subsequently be capable of being separated into its constituents by water entrainment.

Taking these requirements into account, it has also been found that it is preferred to use, as the said third component, an ester of an organic acid, preferably an aliphatic acetate, in which the aliphatic radical derives from an alcohol which itself satisfies the above conditions. On the other hand, since it is advantageous, as stated above, to use, for the decomposition stage, a third component identical to the previously utilized solvent of extraction, one is suggested to use a mixture of alkyl acetate and the corresponding alcohol in these two stages, namely, the extraction stage and the decomposition stage. Thus, in the present invention, the solvent used in the two stages, i.e., in the extraction and in the decomposition, is preferably a mixture of butyl acetate and butanol, or a mixture of isobutyl acetate and isobutanol, in proportions judiciously selected such that the mixture is a good extraction agent and to prevent or favor, depending upon the circumstances, the occurrence of hydrolysis or esterification side-reactions.

Additionally, as it is known that an alcohol can react with an ammonium salt to form an ester, if a maximum yield of free acetic acid is to be obtained, it is necessary to carefully control the proportions of alkyl acetate and alcohol in the third component so as to avoid ester formation at the expense of the ammonium acetate to be decomposed in the presence of an excess of the alcohol. It has been found that the optimum proportions by weight for these mixtures are of the order of 75% of the alkyl acetate and 25% of the corresponding alcohol. In such a mixture, upon termination of the decomposition reaction, the acetic acid concentration is from 10 to 20% relative to the anhydrous mixture, and preferably 12 to 15%.

Thereafter, the acetic acid is separated from the anhydrous third component in a last distillation column, in the presence of water which acts as an entraining agent. The third component is thus recovered in the upper part of the column, by hetero-azeotropic distillation, and is separated, in a water-saturated state, from the aqueous layer and thence is recycled to the decomposition stage. The anhydrous acetic acid is collected from the lower section of the column.

Of course, as in any extraction process, the solvent third component dissolved in the water, from which the acid has been removed and which emanates from the extraction column, must be recovered by distillation; to accomplish this, it is possible to use the heat available at the head of the column for the decomposition of the ammonium acetate and the column for the separation of the anhydrous acid, in accordance with conventional heat recovery techniques, by operating the column for the distillation of the water, and from which the acid has been extracted, under reduced pressure.

The present invention thus makes it possible to obtain anhydrous acetic acid in an highly economical manner.

According to another feature of the present invention, the process for the recovery of the acetic acid is carried out so as to obtain, other than the acetic acid, a greater or lesser amount of alkyl acetate, more particularly of butyl acetate or isobutyl acetate.

As stated above, it is known that it is possible to obtain esters by reaction of an ammonium salt with an alcohol; U.S. Pat. No. 2,565,487 particularly described the preparation of n-butyl acetate from ammonium acetate and n-butanol. Within the context of the present process, it suffices to modify the alcohol/alkyl acetate ratio in the third component at the stage of decomposition of the ammonium acetate. If the alcohol content in the third component charged to the decomposition column is raised to a value sufficiently about 25%, and the functioning of this column is adjusted as a consequence, a certain amount of alkyl acetate is produced besides the acetic acid. Of course, in this case, the portion of the mixture of alkyl acetate and of the corresponding alcohol which is recycled to the stage in which the acetate is decomposed must be readjusted, and supplemented, by adding an amount of alcohol corresponding to the amount of alcohol esterified by the ammonium acetate, so as to maintain a third component of suitable composition in the decomposition column.

The FIGURE of drawing schematically represents apparatus which is well suited for carrying out the process of the invention, and which is given purely by way of illustration and without limitation.

The extracting column 1 operates in countercurrent manner. It is charged with the aqueous solution of acetic acid requiring treatment through the pipeline 2, and the solvent of extraction is fed through the pipeline 3. The acid extract withdrawn from this column through the pipeline 4 is feed for the neutralization and wash column 5 at the base thereof; into the base of this latter column there is also introduced an ammonia solution through pipeline 6, and water is introduced overhead through the pipeline 7. The solvent which has been deacidified by neutralization with ammonia and washing with water is returned to the extraction column through pipeline 8 and thence via the pipeline 3. At the base of the column 5, the aqueous ammonium acetate solution is withdrawn through a pipeline 9 and is collected in a tank 10.

From this tank 10, a certain fraction of ammonium acetate solution is passed through a pipeline 11 to the upper portion of a column 12 wherein saturation with ammonia is effected, the column also being fed, at the base thereof, with recycled gaseous ammonia through a pipeline 13, and is topped with fresh ammonia through a pipeline 14.

The aqueous ammonium acetate solution, enriched with the amount of ammonia required for neutralizing the acetic acid in column 5, is drawn off from the base of the column 12 through the pipeline 6.

A pipeline 15 which conducts feed to the column 16 for the decomposition of ammonium acetate with an aqueous solution of such acetate also emanates from the tank 10. This column 16 at the same time receives, through a pipeline 17 which branches into the pipeline 15, the supply of the third component required for hetero-azeotropic operation and, if necessary, a topping supply of alcohol through a pipeline 18. This column 16, heated at its base by means of an exchanger 19, is equipped at its upper part with a hot decanting tray 20.

The ammonia liberated by thermal decomposition of the ammonium acetate is conveyed through a pipeline 21 into a condenser 22 which is also connected to the column 16 by a reflux pipeline 23, from which branches the pipeline 13 which feeds the saturation column 12 with recovered ammonia.

The water from the aqueous ammonium acetate solution which is hetero-azeotropically entrained by the third component is drawn off from the lower layer of the decanting tray 20 through a pipeline 24 and fed to an attached column 25 heated at its base by an exchanger 26; from the top of this column, the third component and the ammonia which were dissolved in the water are withdrawn in the gaseous state and returned to the column 16 through a pipeline 27, while the purified water is withdrawn through a pipeline 28 into a tank 29 serving as a reserve supply. From this tank 29, the column 5 can be supplied with water through the pipeline 30 and 7 and the acid separation column 31 can be supplied with water through a pipeline 30; furthermore, a pipeline 32 makes it possible to discharge any excess water or, at the start of the operation, to introduce into the tank the amount of water required for initial operation of the installation.

The separation column 31 is fed, through a pipeline 33, with the mixture of acetic acid and third component drawn off from the base of the column 16. The upper region of the column 31 is equipped with a decanting tray 34 and a condenser 35, by means of swan-neck 36 and a reflux pipeline 37. This column 31 is also equipped with a surface heater 38 and a pipeline 39 for laterally withdrawing acetic acid in the vapor phase, pipeline 39 opening into a condenser 40 from which derives the anhydrous acetic acid.

From the decanting tray 34, the organic layer consisting of the third component saturated with water is withdrawn through the pipeline 17 and is thus passed into the decomposition column 16 via the pipeline 15.

Where the process is carried out so as to produce a certain amount of alkyl acetate, a portion of the organic layer withdrawn through the pipeline 17 is taken off through the pipeline 41 in order to feed a conventional installation for the separation and purification of the said alkyl acetate.

A pipeline 42 permits purging to lower the concentration of impurities; the liquid thus taken off can optionally be recycled to the extraction column 1.

At the base of the column 1, the water depleted in acid issues through a pipeline 43, passes through the exchangers 44 and 45 and feeds a distillation column 46 heated at its base by an exchanger 47 and equipped with a tray decanter 48. A pipeline 49 makes it possible to withdraw therefrom the recovered solvent which constitutes the organic layer, and to pass same into an intermediate tank 50 from where it is recycled to the extraction column.

The heat available in the exchangers 22 and 35 can be used for heating the column 46, which is advantageously operated under reduced pressure.

The amount of steam fed to the columns 16, 25 and 31, required to produce 1 ton of purified anhydrous acetic acid, can be expressed by the following equation, which is given by way of example:

$$Q = (10/x) + 12$$

and wherein, $x$ represents the concentration, in percent by weight, of acetic acid in the aqueous solution to be treated, and is between 1 and 3. This amount of steam is at least two to three times lower than the amounts usually required for carrying out the conventional process for the extraction of acetic acid from very dilute aqueous solutions thereof.

In order to further illustrate the present invention and the advantages thereof, the following specific example is given, the same reflecting an embodiment of the process of the invention being continuously carried out in the apparatus of the figure of drawing, and the same being intended only as illustrative and in nowise limitative.

EXAMPLE

Recovery of acetic acid from an aqueous, 1% acetic acid solution.

Referring to the FIGURE of drawing, the extraction column 1 was fed via pipeline 2 on an hourly basis with an amount of aqueous acetic acid solution consisting of 99 tons of water and 1 ton of acid, and, through pipeline 3, with 160.418 tons of a mixture of 153 tons of a third component solvent consisting of 25% of butanol and 75% of butyl acetate, 7.4 tons of water and 0.018 tons of ammonium acetate [these quantities also being per hour, as are the quantities given below].

From the base of the column 1, 102.068 tons of a mixture consisting of 99 tons of water, 3 tons of third component solvent, 0.05 tons of acid and 0.018 tons of ammonium acetate were withdrawn through the pipeline 43. This mixture was conveyed to the solvent exhaustion column 46.

At the top of the column 1, 158.35 tons of acid extract consisting of 7.4 tons of water, 0.95 tons of acetic acid and 150 tons of third component went overhead through the pipeline 4. The acetic acid extraction yield was thus 95%. The concentration of acetic acid relative to the total weight of acetic acid and water in the extract was 11.4%.

This acid extract was next neutralized in the column 5 with an aqueous solution introduced through the pipeline 6 and consisting of 0.265 tons of ammonia, 1.202 tons of ammonium acetate and 4.07 tons of water. At the same time the column 5 was fed, through the pipeline 7, 4.07 tons of water for washing the neutralized third component which subsequently was recycled to the extraction column 1; thus 157.418 tons of a mixture consisting of 150 tons of third component, 7.4 tons of water and 0.018 tons of ammonium acetate were recycled.

At the base of the column 5, 10.544 tons of a solution of 2.404 tons of ammonium acetate and 8.14 tons of water were collected through the pipeline 9. The concentration of potential acetic acid in this solution, relative to the total weight of potential acid and water, was 18.8%. Upon leaving from the tank 10, this solution was equally divided between the column 12, through the pipeline 6, and the column 16, through the pipeline 15.

The column 16 was at the same time fed, via the pipeline 17, with a mixture of 6.86 tons of third component, which here serves as the entraining agent, and 0.33 tons of water. The residence time, in the column, of the components introduced therein was 3 hours and the temperature prevailing in the reaction zone of the column ranged from 105° to 127° C.

The ammonia liberated by thermal decomposition of the ammonium acetate issues from the top of the column 16 and, after passing into the condenser 22, was returned to the column 12, through the pipeline 13, for the purpose of saturating the aqueous ammonium acetate solution recycled from the tank 10, the said column 12 additionally being topped with 0.018 tons of fresh ammonia through the pipeline 14.

The aqueous phase was withdrawn from the tray decanter 22 and fed to the column 25, from the base of which 4.40 tons of water were withdrawn and passed via pipeline 28 to the tank 29. From this tank, 4.07 tons of water were charged into the column 5 through the pipeline 7, for the purpose of washing the solvent in column 5, and 0.33 tons were passed to the separating column 31 through the pipeline 30, to serve as the entraining agent in column 31.

At the base of column 16, a mixture of 0.936 tons of acetic aid and 6.86 tons of anhydrous third component were obtained. This mixture is feed for the separating column 31.

0.936 tons of pure acetic acid were withdrawn from the column 31 through the pipeline 39 and passed into the condenser 40; on issuing therefrom, the material was collected as final product.

The third component saturated with water was withdrawn from the tray decanter and returned to the column 16 through the pipeline 17.

The column 46 for removing solvent from the waters emanating from the extraction column was operated under an absolute pressure of 250 mm Hg. The heat with which it is supplied derives from the condensers 22 and 35. This solvent recovery accordingly took place without an external supply of heat.

The amount of steam which had to be supplied to the base of the column 16, 25 and 31 was, in sum, less than 22 tons per ton of anhydrous acetic acid collected upon exiting from the column 31.

While there have been described and pointed out the fundamental novel features of the invention as applied to the preferred embodiment, those skilled in the art will appreciate that various modifications, changes and omissions in the recovery of acetic acid from dilute aqueous solutions thereof described and illustrated can be made without departing from the spirit of the invention. It is the invention, therefore, to be limited only by the scope of the claims which follow.

What is claimed is:

1. A process for the recovery of acetic acid from dilute aqueous solutions thereof containing from about 0.5 to about 3.0% acetic acid, comprising extracting such a dilute aqueous solution with an organic solvent, neutralizing the acidic extract with aqueous ammonia, whereby there are separated an organic phase and an ammonium acetate containing aqueous phase, withdrawing said aqueous phase, thermally decomposing the ammonium acetate present in said aqueous phase at atmospheric pressure and at a temperature within the range of from about 90° C. to about 130° C. in the presence of an agent capable of forming with water a minimum boiling point hetero-azeotrope, and thence recovering the acetic acid of decomposition.

2. The process as defined by claim 1, further comprising washing the separated organic phase with water and adding the wash water to the said aqueous phase prior to thermal decomposition.

3. The process as defined by claim 1, wherein the temperature is within the range of about 105° to 127° C.

4. The process as defined by claim 1, further comprising recycling the ammonia of decomposition to the zone of neutralization.

5. The process as defined by claim 1 conducted on a continuous basis.

6. The process as defined by claim 1, wherein the step of thermally decomposing said ammonium acetate comprises thermally decomposing said ammonium acetate in a distillation zone in the presence of an agent capable of forming with water a minimum boiling point hetero-azeotrope.

7. The process as defined by claim 6, wherein the azeotropic agent is such as to form, with water, a heteroazeotrope of highest water content, which has a high boiling point to permit of its ready and complete separation from ammonia, which maintains the ammonium acetate in solution in the reaction zone bottoms, which is incapable of irreversibly reacting with the ammonia under the conditions of decomposition, and which forms, with acetic acid, a homogenous liquid admixture capable of separation into its individual components upon entrainment with water.

8. The process as defined by claim 7, wherein the azeotropic agent comprises an ester of an organic carboxylic acid.

9. The process as defined by claim 8, wherein the ester is a lower alkyl acetate.

10. The process as defined by claim 6, wherein the organic solvent of extraction serves as the azeotropic agent.

11. The process as defined by claim 10, wherein the organic solvent and the azeotropic agent comprise a mixture of a lower alkyl acetate and the corresponding lower alkanol.

12. The process as defined by claim 11, wherein the mixture is selected from the group consisting of (1) n-butyl acetate and n-butanol, and (2) isobutyl acetate and isobutanol.

13. The process as defined by claim 11, wherein the mixture comprises about 75% by weight of lower alkyl acetate and about 25% by weight of lower alkanol.

14. The process as defined by claim 6, further comprising withdrawing ammonia and water overhead of the distillation zone, and withdrawing dehydrated azeotropic agent and acetic acid from the base thereof.

15. The process as defined by claim 6, further comprising recovering, by distillation, the solvent dissolved in the aqueous residuum of extraction, and thence recycling such solvent to the extracting step.

16. The process as defined by claim 6, further comprising separating the acetic acid from the anhydrous azeotropic agent by distillation in the presence of water as an entraining agent.

17. The process as defined by claim 16, further comprising recycling the separated azeotropic agent to the distillation zone.

18. The process as defined by claim 16, further comprising a lower alkanol azeotropic agent.

* * * * *